United States Patent [19]
Murnick

[11] Patent Number: 5,818,580
[45] Date of Patent: Oct. 6, 1998

[54] SIMULTANEOUS MULTISAMPLE ANALYSIS AND APPARATUS THEREFOR

[75] Inventor: Daniel E. Murnick, Bernardsville, N.J.

[73] Assignee: Rutgers, The State University, Piscataway, N.J.

[21] Appl. No.: 615,036

[22] Filed: Mar. 12, 1996

[51] Int. Cl.$^6$ ............................................. G01J 3/30
[52] U.S. Cl. ........................... 356/311; 356/308; 356/315
[58] Field of Search .................................. 356/311, 308, 356/315

[56] References Cited

U.S. PATENT DOCUMENTS 5,361,772 11/1994 Murnick et al. .
5,394,236  2/1995 Murnick .

OTHER PUBLICATIONS

Alimenterics Inc, "The LARA System; Laser Assisted Ratio Analyzer" pp. 1–4, 1995.
Abstract, Murnick et al., "Stable Isotope Analysis of Breath Using the Optogalvanic Effect," SPIE Conference, Optical Diagnostics of Living Cells and Biofluids, 1996.
Murnick et al., "Stable Isotope Analysis of Breath Using the Optogalvanic Effect," paper, proceedings of the SPIE Conference, Optical Diagnostics of Living Cells and Biofluids, 1996.

*Primary Examiner*—K. Hantis
*Attorney, Agent, or Firm*—Lerner, David, Littenberg, Krumholz & Mentlik

[57] ABSTRACT

Analytical apparatus and methods for processing multiple samples simultaneously. Radiation such as laser light desirably including plural wavelengths is directed through multiple samples simultaneously, as by directing a beam of radiation along a single path through all of the samples. Response to each wavelength is monitored by monitoring an induced effect, other than the intensity of the applied radiation itself. Useful signal-to-noise ratios are obtained with low absorption in each sample. One sample desirably is of known composition, and serves as an internal calibration standard.

27 Claims, 2 Drawing Sheets

SIMULTANEOUS MULTISAMPLE ANALYSIS AND APPARATUS THEREFOR

The present invention relates to methods and apparatus for analyzing a plurality of samples such as gas samples by exposure to radiation such as laser light.

Analytical test methods involve transmission of radiation through a sample of the material to be tested, commonly referred to as a "analyte". For example, some photometric tests measure the amount of light absorbed by a sample at a particular wavelength associated with a particular substance. If a particular chemical substance strongly absorbs red light, the amount of the substance in the sample can be determined by directing a beam of red light through the sample. A photodetector measures the amount of red light remaining in the beam after passing through the sample. The greater the content of illumination, the less red light remains in the beam. Many variations of this basic scheme are known by using different wavelengths of radiation. Because the amount of light reaching the photocell depends on the performance of a light source, such as the amount of illumination provided by a lamp, a reference beam from the lamp may be directed along the same path when the sample is removed to provide a reference or calibration reading, or along a separate path to a separate photodetector so as to provide a continuous calibration reading. Also, where the analyte may contain several different substances, each of which absorbs light at a different wavelength, the sample can be tested at each of these different wavelengths to determine the amount of each substance. Typically, photometric measurements of this type are used to monitor the amounts of different chemical substances, i.e., different elements or compounds in the sample.

As described in U.S. Pat. No. 5,394,236 of Daniel E. Murnick, another measuring technique can be used to determine the amounts of particular atomic isotopes present in a sample. Isotopes are different forms of the same chemical element, having an atomic nuclei of different masses. For example, naturally occurring carbon consists predominantly of $^{12}C$, i.e., carbon having an atomic mass of 12 atomic mass units ("amu"). Other isotopes of carbon are $^{13}C$ and $^{14}C$ having masses of 13 or 14 a.m.u. respectively. $^{14}C$ is radioactive, whereas $^{13}C$ and $^{12}C$ are stable, nonradioactive materials.

Certain preferred methods taught in the '236 patent involve directing one or more beams of light through a sample which includes multiatomic moieties, such as carbon dioxide molecules or ions containing different isotopes. The preferred methods include the same step of providing the analyte in a condition such that some of the isotope-bearing species in the analyte are present in excited states. Typically, the analyte is maintained in this excited condition by maintaining the analyte in an ionized gas or "plasma". At least some of the electrons in the molecules or ions are at energy levels higher than the energy levels occupied in the ground or normal state of the isotope-bearing species. Such excited states have associated "transition energies" corresponding to the energy released upon transition from the excited state to a lower state, or absorbed upon the reverse transition, from the excited state to another, higher energy state. Most preferably, the isotope-bearing species are multiatomic moieties such as multiatomic ions or molecules. The transition energies are different for isotope-bearing species incorporating different isotopes as, for example, $^{13}CO_2$ and $^{12}CO_2$. In the preferred methods according to the Murnick '236 patent, radiation such as light incorporating plural wavelengths corresponding to the transition energies of the excited isotope-bearing species is applied to the sample. Light at each wavelength interacts with the species including one isotope, and does not interact substantially with the species including the other isotope.

By measuring response of the analyte to the applied radiation at the different wavelengths, one can determine the amounts of the different isotopes present in the sample. In particularly preferred methods according to the Murnick '236 patent, the response of the sample is measured by monitoring changes in the electrical impedance of the plasma caused by light at the different wavelengths, commonly referred to as the "optogalvanic effect". As disclosed in the '236 patent, light at plural wavelengths may be provided by one or more lasers in a single beam with light at different wavelengths varying at different frequencies. For example, light at a wavelength associated with $^{13}CO_2$ may be turned on and off at a first modulation frequency, whereas light at the wavelength corresponding to $^{13}CO_2$ may be turned on and off at a second modulation frequency. The electrical signal corresponding to the optogalvanic effect includes two separate components, one at the first modulation frequency representing the amount of $^{12}CO_2$ and another at the second modulation frequency representing the amount of $^{13}CO_2$. These can be electronically separated from one another and measured to provide a pair of signals which represents the relative amounts of the two isotopes.

The preferred methods according to the Murnick '236 patent provide numerous advantages over other methods used for determining the amount of different isotopes in a substance. Methods and apparatus according to the '236 patent can be reapplied to many different analytes for many different purposes. However, one especially useful application of these methods is in medical testing. Various medical and scientific procedures require determination of the relative amounts of different isotopes. In certain medical tests, a test compound includes a rare isotope such as $^{13}C$ in the compound. The test compound is administered to the subject. The amount of the rare isotope which appears in the subject's bodily fluids or breath depends upon the subject's ability to metabolize or process the test compound. Thus, the amount of the rare isotope or the ratio of the more isotope such as $^{13}C$ to the more common isotope such as $^{12}C$ indicates the subject's ability to metabolize the test compound. One such test involves the administration of $^{13}C$ labeled urea to the subject by mouth. If the subject has *heliobacter pylori* bacteria present in the gastrointestinal tract, the $^{13}C$ will be incorporated into the carbon dioxide produced by the patient and exhaled as part of the patient's breath. Thus, the ratio of $^{13}C$ to $^{12}C$ in the patient's breath indicates whether or not *heliobacter pylori* are present. Other, breath tests involve administration of other compounds labeled with isotopes of carbon or with isotopes of other elements.

Apparatus and methods for isotopic analysis of substances face several conflicting requirements. The analytical apparatus should be capable of processing as many samples as possible per unit time. Typically, the sample chamber which holds the sample during analysis is a permanent component of the instrument. Therefore, a time-consuming process of purging the sample chamber and introducing a new sample must be performed between each test in a series of tests. Even when the actual test can be performed rapidly, the overall throughput or sample process rate of the instrument is limited by this procedure.

Although it would be possible to increase the rate of testing by duplicating the testing instrument, this solution would be costly. Moreover, it would introduce an additional source of variation in that test readings would require cross-calibration to match the characteristics of the different instruments with one another, so that a reading obtained on one instrument would be directly comparable to data obtained on another instrument. Even where only one instrument is employed, its calibration may drift or change from time to time. To provide useful comparison between samples, the instrument must be repeatedly recalibrated by testing known samples. This, in turn, further reduces the time available for testing real samples. These problems are particularly important in the case of tests where analyses of different samples are compared to one another. In certain medical tests, plural samples of bodily fluids are taken from a particular subject at different times. For example, in the urea breath test as discussed above, samples of breath may be collected before administration of the labeled urea and at one or more times after administration. Evaluation of the test may involve comparison between the "before" and the "after" samples. It is important that any effects of variation between instruments, or variation of a single instrument from time to time neither magnify nor diminish any differences between the plural samples. Accordingly, there have been substantial needs for improvements in methods and apparatus for testing analytes by exposure to radiation.

SUMMARY OF THE INVENTION

The present invention addresses these needs.

One aspect of the present invention provides a method of analyzing an analyte including the steps of maintaining a plurality of separate samples of the analyte. The method according to this aspect of the invention further includes the step of directing radiation including a wavelength corresponding to a transition energy of each such species through the plural samples by directing one or more beams of radiation through all of the samples in an upstream to downstream order. Typically, the samples are maintained in separate chambers arranged on a path, and the beam is directed along the path, to pass through all of the chambers in sequence and thereby simultaneously expose all of the samples to radiation essentially simultaneously. Methods according to this aspect of the invention further include the steps of monitoring the interaction between the applied radiation and the samples by monitoring an induced effect which the applied radiation causes in the samples. As used in this disclosure, the term "induced effect" means a phenomenon other than the change in radiation intensity at the applied wavelengths. Induced effects include the optoacoustic effect; stimulated fluorescence and the optogalvanic effect.

Monitoring of an induced effect can provide useful signal-to-noise ratios even where only a small fraction of the applied radiation is absorbed by each sample. Most preferably, the applied radiation undergoes little or no net change in intensity as it passes through each sample chamber. The samples at the downstream end of the path receive essentially the same radiation intensity as the samples at the upstream end. Moreover, any variation in absorption by the samples at the upstream end of the path produces only a minute change in intensity applied to the samples at the downstream end. For all practical purposes, the radiation intensity applied to the samples at the downstream end can be regarded as independent of the absorptivity of the samples at the upstream end. The step of directing the beam may further include the step of reflecting the beam through the chambers, so that the beam passes in both upstream and downstream directions through the chambers one or more times. This further reduces differences in the applied radiation intensity between samples at the upstream end of the path and samples at the downstream end of the path.

By comparison, where the interaction is monitored in the conventional manner, by monitoring the intensity of the applied radiation after passage through the sample, the signal representing the interaction of the applied radiation with the sample is the difference between the intensity of the applied radiation and the intensity of the radiation after passage through the sample. Any noise or fluctuation in the applied radiation appears as noise in the signal representing the interaction. This noise obscures the signal representing the interaction. To provide a useful signal-to-noise ratio, each sample must absorb a substantial amount of the applied radiation, and the amount of radiation absorbed by each sample must vary substantially depending upon the composition of the sample. For these reasons, common photometric instruments do not normally direct a single beam of light through plural samples in series.

The ability to direct the light through plural samples in series in methods according to this aspect of the invention leads to very significant benefits. Because a single beam can be directed through several samples simultaneously on a single optical path, the number of samples processed per unit time or throughput rate of the instrument can be multiplied several fold. This can be accomplished using a simple optical arrangement, including only a single optical path. Because several samples can be exposed to the radiation in a single, simultaneous operation, variation in operation of the radiation-producing elements of the instrument will not affect the comparisons between these samples. In one particularly preferred embodiment, the plural samples tested simultaneously using a single beam of light may include samples taken from a single patient in a medical test as, for example, breath samples taken from a single patient at different times, such as before and after administration of a test substance. This allows a particularly precise comparison between the results for the various samples.

Preferably, one of the plural samples is a sample of known composition. The results observed within the known composition serve as a calibration reference. In this arrangement the instrument is calibrated every time a sample is measured. Any change in the characteristics of the incident beam of radiation is detected. Therefore, the results observed within the known samples can be corrected to compensate for any such change. Because the calibration can be performed simultaneously with tests of unknown samples, it does not substantially decrease sample throughput.

Most preferably, the samples are maintained in a condition in which at least one species to be detected is in an excited state, and the wavelengths of the applied radiation correspond to the transition energy of each such species in its excited state. Preferably, the samples are maintained in plasmas. The step of monitoring an induced effect preferably includes the step of monitoring the optogalvanic effect caused by the applied radiation. The term "optogalvanic effect" refers to the change in electrical impedance of a plasma caused by applied radiation. The optogalvanic effect provides a readily measurable electrical signal even where the plasma absorbs only a small portion of the applied radiation. Moreover, where the applied radiation includes a wavelength corresponding to a transition energy of a species in an excited state, each sample will emit some radiation at that wavelength through a process known as stimulated emission. The relationship between the amount of radiation emitted and the amount absorbed will depend on properties of the plasma such as the proportion of atoms or molecules of the species which are in the excited state. The net effect on the beam passing through each sample may be either a decrease in intensity or an increase in intensity. Preferably, however, the amount of radiation emitted is slightly larger than the amount absorbed, so that the net increase in intensity of the beam caused by passage through a sample compensates for attenuation caused by passage of the beam through the walls of the sample chamber. Stated another way, the sample itself may provide an intensity gain of slightly more than unity, whereas the sample and chamber together may have an intensity gain of approximately unity.

Most preferably, the beam of radiation directed through the plural samples includes a plurality of wavelengths corresponding to transition energies of a plurality of species which may be present in the analyte samples. Desirably, the method also includes the step of comparing the responses for each sample at each wavelength to the response of the same sample at the other wavelength to measure the relative abundances of the various species in each such sample. For example, where the various wavelengths correspond to transition energies of species incorporating different isotopes, the method can provide a measure of the relative abundances of the different isotopes in each sample.

According to a further aspect of the invention, a method of analyzing analytes may include the steps of maintaining plural separate samples of the analyte and directing radiation including plural wavelengths corresponding to transition energies of a plurality of species through the plural samples so that radiation passes from a common source of radiation through all of the samples substantially simultaneously and hence, all of the samples will be exposed to substantially the same radiation despite any drift or variation in the performance of the radiation source. Methods according to this aspect of the invention further include the steps of monitoring the response of the samples to the radiation to determine a response for each of the wavelengths, and comparing the responses for each sample at each wavelength to other responses of the same sample at the wavelengths to produce a measure of the relative abundances of the species in each such sample. This step may be performed by determining a response ratio between the magnitudes of responses of each sample to different wavelengths. Here again, the samples may include at least one reference sample having known composition and at least one unknown sample. The method may include the step of adjusting the measure of relative abundance for each unknown sample based upon the responses for the reference sample. This step may be performed by computing a ratio between the aforesaid response ratio for the unknown sample and the response ratio for the standard sample. As further discussed below, such ratiometric calculations can cancel the effects of changes in instrument conditions. Methods according to this aspect of the invention may include the other features discussed above. Thus, the step of monitoring responses of the samples to the applied radiation may include the step of monitoring an induced effect. Here again, the samples may be maintained in a condition wherein the species to be determined are in excited states. The step of directing radiation through the plural samples simultaneously may include the step of directing a beam of radiation through the plural samples so that the same beam passes through all of the samples in sequence.

Methods according to the foregoing aspects of the present invention most preferably include the step of loading the plural samples into plural chambers simultaneously. Where the samples are gaseous, the loading step may include the steps of evacuating a plurality of sample chambers simultaneously; admitting various samples to individual evacuated chambers simultaneously and bringing the various samples to a preselected pressure by withdrawing portions of each sample from the respective chambers simultaneously.

Further aspects of the present invention provide analytical apparatus. Apparatus according to one aspect of the invention includes a plurality of sample chambers arranged along an optical path in an upstream to downstream order, each such sample chamber having an upstream end and a downstream end, and transparent walls at the upstream and downstream ends. The apparatus may include a frame, and the chambers may be permanently mounted to the frame in alignment with one another along the optical path. The apparatus further includes means introducing analyte into at least one of the chambers. The apparatus further includes a source of radiation at one or more preselected analysis wavelengths and means for directing such radiation in a beam along the upstream to downstream extent of the path, through all of the sample chambers. Additionally, the apparatus includes means for monitoring an induced effect caused by the radiation to thereby monitor the response of analyte disposed within each chamber to such radiation. Most preferably, the source of light may include one or more lasers. The apparatus desirably includes excitation means for applying energy to analyte disposed within each chamber so as to bring species contained within such analyte into excited states. The excitation means may include means for applying electrical energy such as radio frequency energy to samples contained in the various chambers. Thus, the excitation means may include one or more RF coils connected to a common source of excitation energy such as a common radio frequency power unit.

The apparatus may further include loading means for loading samples into the various chambers. The loading means may be operable in cycles, so as to load all of the chambers with different samples in a single cycle. Preferably, the loading means include means for loading a standard analyte of known composition into one or more of the chambers on each cycle. Alteratively, one of the chambers may have a standard analyte permanently sealed therein. Apparatus in accordance with this aspect of the present invention can be used to perform the methods discussed above.

These and other objects, features and advantages of the present invention will be more readily apparent from the detailed description of the preferred embodiments set forth below taken in conjunction with the accompanying drawings.

DETAILED DESCRIPTION OF THE PREFERRED EMBODIMENT

Apparatus in accordance with one embodiment of the invention includes a frame 10, a first laser 12 and a second laser 14 mounted on the frame. Each of the lasers is a conventional gas laser. As described, for example, in the aforementioned '236 patent, a conventional gas laser includes a tube filled with a gas mixture, discharge electrodes adapted to create an electrical discharge within the tube and optical components such as Brewster or polarizing windows and a partially reflective output mirror. The first laser 12 has a tube filled with a mixture of $^{13}CO_2$ in a carrier gas such as a helium—nitrogen mixture. Its optical components are arranged so that light at a wavelength corresponding to a transition energy of excited-state $^{13}CO_2$ ions, desirably at about 11200 nm, is amplified within the tube. The first laser 12 also includes a power source 13 for applying an excitation potential between the electrodes and creating a discharge within the tube. Thus, laser 12 is adapted to emit the first beam 16 of infrared light at the first wavelength, corresponding to a transition energy of excited-state $^{13}CO_2$ ions. The second laser 14 includes similar structures, but its gas tube is filled with a mixture containing $^{12}CO_2$ in the inert carrier gas, and its optical components are arranged to amplify light at a second wavelength, desirably about 10600 nm, corresponding to a transition wavelength of excited-state $^{12}CO_2$ ions. Second laser 14 also includes a power source 15 adapted to apply an excitation voltage across the electrodes in the tube. These known elements are adapted to cooperate with one another to emit a second beam 18 of infrared radiation consisting essentially of light at a second wavelength corresponding to the transition energy of excited-state $^{12}CO_2$ ions.

The apparatus further includes a directing mirror 20 adapted to redirect beam 18 and a combining optics 22 adapted to combine the two beams in a single beam 24. The optical components, including the combining optics 22, are arranged to attenuate the beam from second laser 14 (at the second wavelength associated with $^{12}CO_2$) to a greater degree than they attenuate the beam from first laser 12 (at the first wavelength associated with $^{13}CO_2$). For example, the combining optics may include a partially-transmissive, partially reflective element arranged so that the beam from second laser 14 is transmitted through the element, whereas the beam from first laser 12 is reflected from it. The characteristics of this element may be selected so that the transmitted beam undergoes substantially greater attenuation than the reflected beam. Thus, if the first and second lasers produce approximately equal intensities, the combined beam 24 will have substantially greater intensity at the first wavelength than at the second wavelength. As further discussed below, this arrangement compensates for the greater abundance of the species associated with the second wavelength in the samples to be analyzed.

An upstream end mirror 26 is adapted to receive combined beam 24 and to direct it along an optical path coincident with axis 28. A downstream end mirror 30 is provided at the downstream end of path 28 for reflecting the beam back towards the upstream end, i.e., back towards mirror 26. All of the mirrors and the optical components of the laser are mounted, directly or indirectly, to frame 10 and hence maintained in alignment with one another by the frame. Additional, conventional optical components such as collimating lenses, filters and the like may be incorporated in lasers 12 and 14, or may be positioned along the various beam paths. These may be used, in the conventional manner, to provide a well-focused, collimated beam along path 28.

Four sample cells 32 are mounted to frame 10 on optical path 28. Sample cell 32a is a substantially closed container defining an interior volume and having a port 34a connected to the interior volume. Sample cell 32a has a transparent upstream end wall 36a and a transparent downstream end wall 38a. The term "transparent" is used herein the ordinary sense to indicate that the end walls transmit a substantial proportion of radiation at the first and second wavelengths. However, even transparent end walls typically attenuate the radiation to some degree. The cell is aligned so that end wall 36a and 38a extend generally perpendicular to the upstream to downstream direction of optical path 28. Sample cell 32a is formed from one or more dielectric materials. For example, the entire cell, including the end walls 36 and 38 may be formed from quartz or other glasses. The other chambers 32b, 32c and 32d have similar features. The chambers are arranged in a row, on the common axis 28 of the path, with the end walls of each chamber facing in the upstream and downstream directions.

A coil 40 is provided in proximity to each chamber 32. Each coil is electrically connected to a separate excitation and detection unit 42. Each excitation and detection unit includes a conventional source 43 of alternating potential at radio frequencies ("RF") connected in a circuit with the associated coil 40. Each unit 42 also includes a conventional detector 45 for monitoring current and voltage across the coil in the circuit, and for providing a signal representing the electrical impedance of a gas discharge inside the associated chamber 32. The signal outputs from excitation and detection units 42 are connected by conventional electronic means, symbolized by a bus 48 to a signal processing unit 50. Signal processor 50 is adapted to convert the analog signals from detection units 45 into digital signals. The signal processor thus includes conventional amplification, filtering and analog-to-digital conversion equipment. The digital outputs from signal processor 50 are connected via digital data bus 52 to a control computer 54. The control computer may include generally conventional computer elements such as a central processing unit, data storage devices including random access memory and mass storage memory, as well as an internal data bus. The computer is also equipped with output control drivers 56 and 58 adapted to connect with control inputs on the power supplies 13 and 15 of lasers 12 and 14. The output control drivers may be conventional computer interface cards, and may be connected to the control inputs of the lasers through conventional control linkages. The computer is also connected to output communication equipment 60 such as a display screen, printer, data storage device such as a disk drive or tape drive or a computer network. The output device is arranged so that results derived by computer 54 may be displayed in human readable form, stored for later retrieval or both. The link is configured so that computer 54 can command lasers 12 and 14 to vary their light output. Typically, this is accomplished by varying the power input to the laser. Accordingly, the internal power supplies 13 and 15 of the lasers are adapted to receive commands from the computer and to vary the power supplies to the electrical discharge in accordance with such commands.

Figure 2:
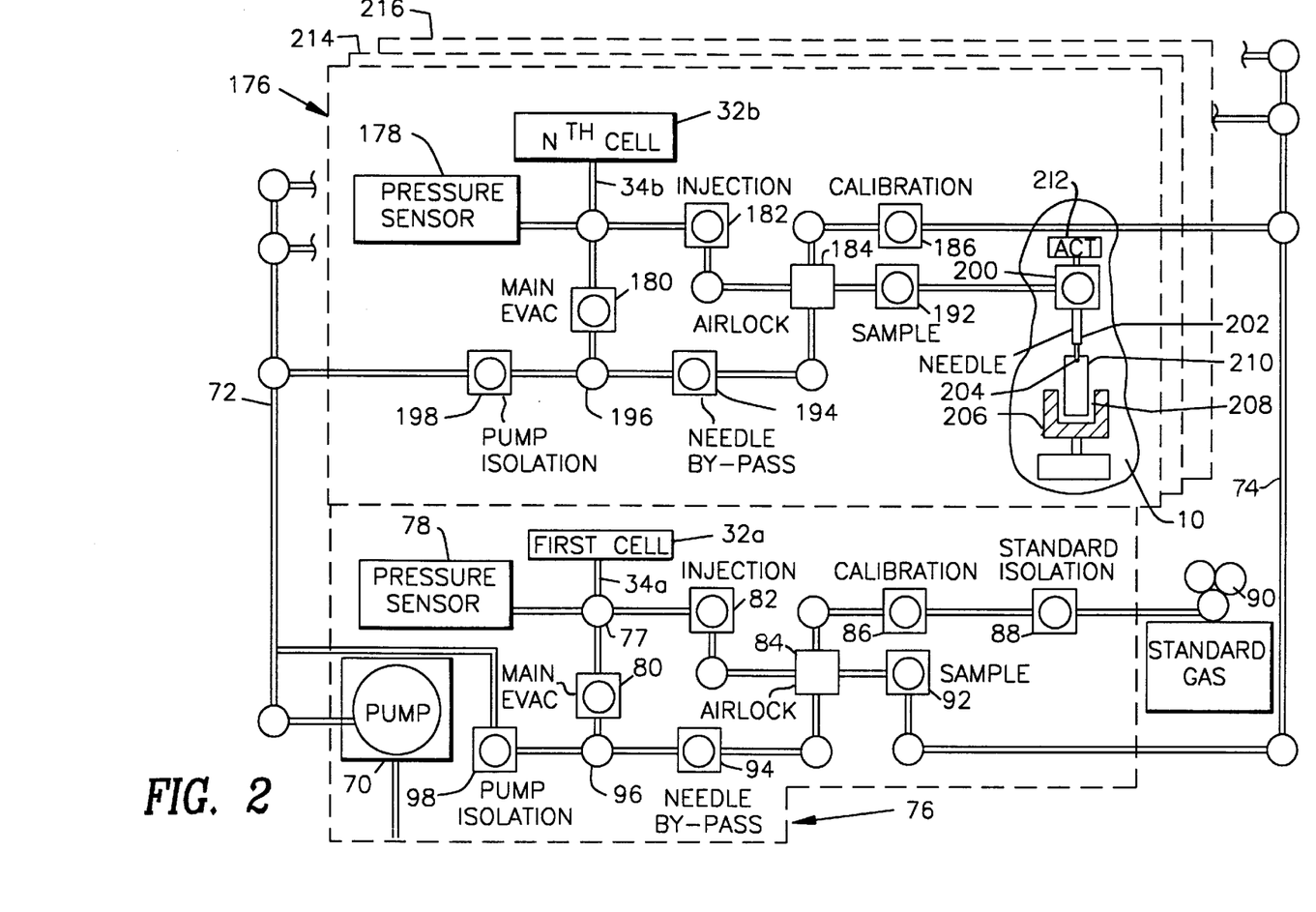
FIG. 2 is a further diagrammatic view depicting additional portions of the apparatus illustrated in FIG. 1.

The apparatus further includes a sample handling and piping system depicted in FIG. 2. This system includes a vacuum pump 70, which may incorporate a conventional vacuum reservoir and a vacuum manifold 72 connected to the suction port of the pump. A standard-handling manifold 74 is also provided. The port 34a of the first chamber 32a is connected to a first-chamber subsystem 76. Subsystem 76 includes a node directly connected to port 34a of the chamber and a pressure sensor 78 connected to node 77. A main evacuation valve 80 and an injection valve 82 are also connected to node 77. Injection valve 82 is a solenoid-actuated valve adapted for rapid on-off cycling and arranged to move from full-open to full-close within a few milliseconds. Injection valve 82 in turn is connected to one port of a multiport, multiposition valve or "air-lock" 84. A further port valve 84 is connected to a calibration valve 86, which in turn is connected to a standard source isolation valve 88. Standard source isolation valve 88 is connected to a source 90 of a standard gas having known concentrations of $^{13}CO_2$ and $^{12}CO_2$. The source may be a conventional tank filled with the standard gas. The tank is equipped with conventional pressure regulating devices adapted to provide the standard gas under a preselected pressure, desirably about 2 psi (about 14 KPa). A further port multiport valve 84 is connected to a sample valve 92, which in turn is connected to the standard manifold 74. Yet another port on multiport valve 84 is connected through a needle bypass valve 94 to a node 96 which in turn is connected to the main evacuation valve 80 and to one side of a pump isolation valve 98. The pump isolation valve is connected to vacuum manifold 74. The output of the vacuum pump is connected to waste.

Figure 1:
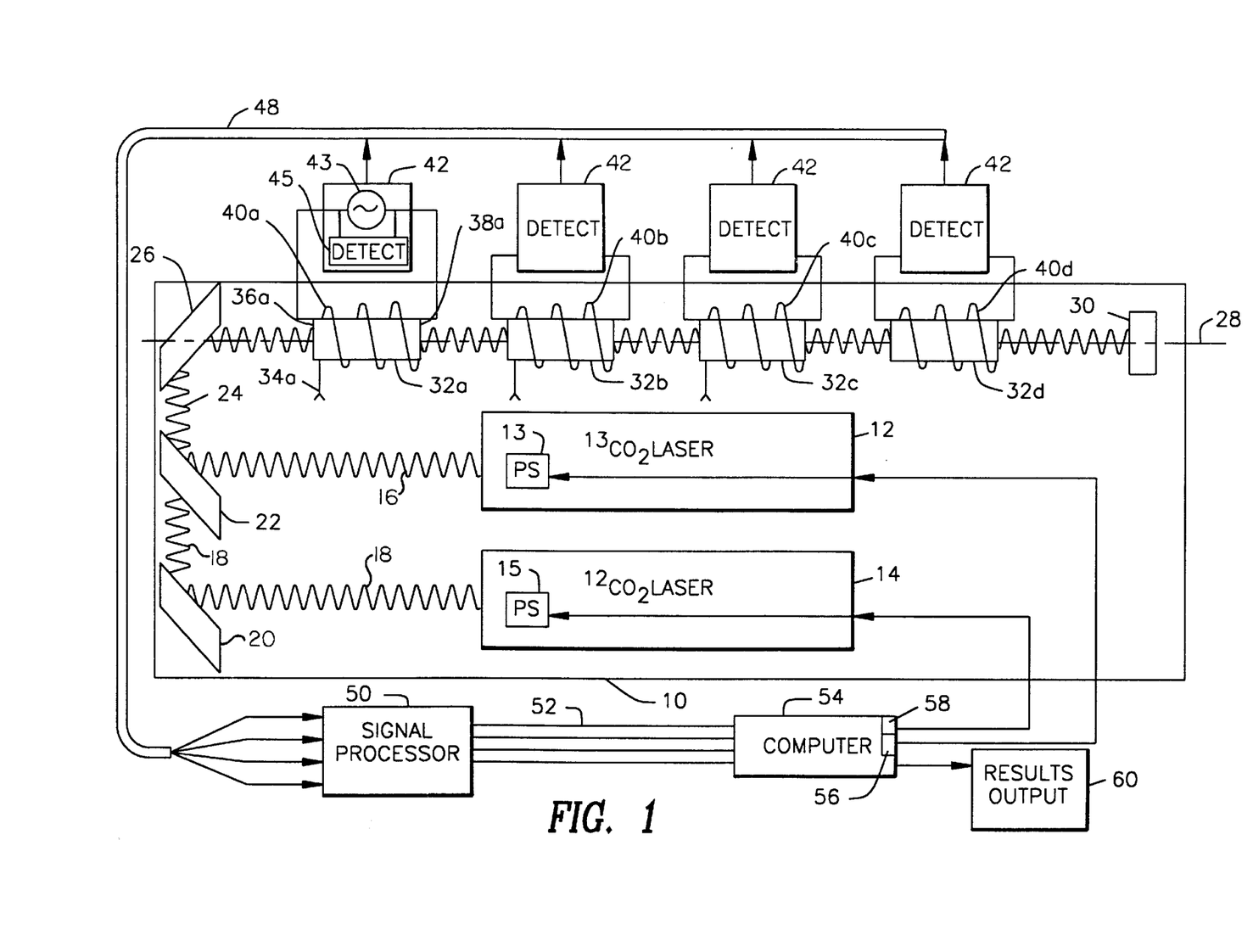
FIG. 1 is a diagrammatic view depicting portions of apparatus in accordance with one embodiment of the invention.

The port 34*b* of the second chamber 32*b* is connected to a generally similar subsystem 176 including pressure sensor 178, main evacuation valve 180, injection valve 182, multiport valve or airlock 184, calibration valve 186, sample valve 192, needle valve 194 and pump isolation valve 198 connected to a vacuum manifold 72. However, the calibration valve of local system 176 is connected to standard manifold 74. Also, the sample valve 192 of subsystem 176 is connected to a needle inlet valve 200. The needle inlet valve in turn is connected to a small, sharpened hypodermic-type needle 204. The needles of the various local subsystems 176, 214 and 216 are mounted on a common actuator 212 for movement relative to frame 10. To allow movement of the needles, each needle is connected by a flexible capillary tube 202 to the associated inlet valve 200. A sample holder 206 is mounted to the frame 10 of the apparatus. Sample holder 206 has a generally cylindrical receptacle 208 adapted to receive a vessel containing a gas sample, such as a breath sample to be analyzed. The sample holders of the various subsystems may be formed as portions of a turntable or other conveyor for moving vessels. The vessel 210 may be a breath collection device of the type described in U.S. Pat. No. 5,361,772, the disclosure of which is hereby incorporated by reference herein. As further disclosed in the '772 patent, such a vessel includes members defining a chamber and a puncturable septum formed as part of one end wall of the vessel. Cell 32*c* (FIG. 1) is connected to a local subsystem 204 identical to subsystem 176, whereas cell 32*d* (FIG. 1) is connected to a further local subsystem 216, also identical to subsystem 176.

All of the valves are linked to computer 54 (FIG. 1) via conventional control interfaces incorporated in the valves and/or in the computer so that each valve can be commanded to open or close by the computer. Also, pressure sensors 78,178 and the corresponding pressure sensors of subsystems 214 and 216 are connected to computer 54 through further conventional interfacing equipment so that the computer can receive data from the pressure sensors.

In a process according to one embodiment of the invention, the system is evacuated by vacuum pump 70 and purged with the standard gas from source 90. In the purging process, the computer may actuate various valves in sequence so as to connect all portions of the system to the vacuum pump and to the standard gas source.

After purging, the system begins cyclic operations. Each cycle includes the step of evacuating the chambers and pressure sensors; loading the chambers and pressure sensors with gases and adjusting the pressure within the various chambers to a preselected pressure. In the evacuation stage of each cycle, the main evacuation valves 80,180 and pump isolation valves 98,198 are opened whereas all other valves are closed, so that all chambers 32*a*–32*d* are evacuated simultaneously. This operation continues until the pressures in the chambers drop below a preselected evacuation pressure, desirably about 0.3 Torr. The pressure detected by sensor 78 associated with the first cell 32*a* can be used as representative of all chamber pressures at this stage. When it drops below the preselected evacuation pressure, the evacuation stage is terminated. Next, gas is loaded into all of the cells simultaneously. Valves 86 and 88 are actuated to connect standard source 90 to the injection valve 82 of the first subsystem. Actuators 212 move all of the needles of 204 subsystems 176, 214 and 216 towards holder 206 thereby engaging the puncturable septum of a sample container 210 with each needle 204. Valves 192,200 and 184 are actuated to connect the needle 204 of system 176 to injection valve 182, whereas the corresponding valves of systems 214 and 216 are also actuated in the same manner. Thus, the injection valves 82,182 and the similar valves of systems 214 and 216 are connected to sources of gases for admission to chambers 32. The computer then actuates each of the injection valves repeatedly for a preselected pulse interval on each repetition. After each repetition, the computer acquires the signal from the associated pressure sensor. If the pressure indicated by the sensor signal for a particular subsystem exceeds a preselected loading pressure, the computer system terminates cyclic operation of the injection valve of that subsystem. In this operation, the injection valves of the various subsystems are treated independently. Repeated cycling of one subsystem may terminate before the others.

In the next stage, the multiport valves 84,184 of the various subsystems are actuated to connect each injection valve 82,182 through the associated needle bypass valve 94,194 and pump isolation valve 98,198 to the vacuum pump 70. At this stage of the operation, the main evacuation valves 80,180 are closed. The system again repetitively pulses the injection valve 82,182 of each subsystem while continually reading the signal from the associated pressure sensor of each subsystem. When the pressure indicated by the sensor of a particular subsystem reaches a desired set point pressure, cyclic operation of the injection valve is terminated. Because the needle bypass valves 94,194 introduce relatively high resistance to flow, each pulse of the injection valves produces only a small change in the pressure within the associated chamber 32. This stage thus serves as a fine adjustment of the pressures in the various chambers. At this point, the gas within the chamber is at the proper set point pressure for testing as discussed below.

In a variant of this cyclic procedure, the loading step is replaced by a reference gas loading step. In the reference gas loading step, the standard gas source 90 is connected through multiport valve 84 and sample valve 92 of the first-chamber subsystem to manifold 74 and is further connected by multiport valve 84 to the injection valve 82 of the first-chamber subsystem. At the same time, calibration valve 186 and multiport valve 24 are actuated to connect manifold 74 to injection valve 182 of each subsystem 176, 214 and 216. Injection valves 82,182 are held open whereas the calibration valve 86 of the first-chamber subsystem is pulsed repeatedly. Computer 54 monitors the pressure in the first chamber by monitoring the reading from sensor 78. When this pressures the predetermined loading pressure, the loading step terminates. After the sample gas loading step, the pressures within he chambers are adjusted by evacuation through needle bypass valves 94,194 as discussed above. This sample gas loading step can be used during a reference cycle as further discussed below.

The instrument can be operated in alternating reference and sample cycles. In each reference cycle, all of chambers 32 are filled with standard gas from source 90 and adjusted to the preselected set point pressure in the manner described above. During each sample cycle, chamber 32a is filled with the standard gas, whereas each of chambers 32b, 32c and 32d receives a sample of a different unknown gas. Where the gases are samples collected from a medical patient, the unknown gases supplied to chambers 32b, 32c and 32d may be samples collected from the same patient at different times. The unknown gases may be breath samples collected from the patient before administration of a 13C-labeled test compound, at a first time after such administration and at a second time after administration. The excitation and detection units 42 supply RF power to coils 40, thereby converting the gas in each chamber to a plasma. The computer commands laser 12 to provide beam 16 with light at the first wavelength corresponding to the transition energy of $^{13}CO_2$, modulated at a first modulation frequency, desirably about 50 to about 100 Hz, and commands laser 14 to provide beam 18 with light at the second wavelength corresponding to the transition energy of $^{12}CO_2$, modulated at a second modulation frequency, desirably about 100 to about 200 Hz. Preferably, the modulation frequencies are not integral multiples of one another. Each unit 42 detects the electrical impedance of the plasma in the associated chamber 32 and provides a signal representing such impedance to computer 54 through signal processor 50. All of units 42 are actuated to detect the signals associated with all of chambers 32a–32d simultaneously.

The impedance signal for each chamber will include a first component of magnitude $S_{13}$ at the first modulation frequency representing the optogalvanic effect of the light at the first wavelength, and a second component of magnitude $S_{12}$ at the second modulation frequency representing the optogalvanic effect of the light at the second wavelength.

Light at the first wavelength interacts with $^{13}CO_2$ but does not substantially interact with $^{12}CO_2$. The first signal magnitude $S_{13A}$ for chamber 32a is given by:

$$S_{13A} = P_{13A} M_{13A} W_{13A} \quad (1)$$

Where:

$P_{13A}$ is the partial pressure or molecular concentration of $^{13}CO_2$ within chamber 32a;

$W_{13A}$ is the beam power at the first wavelength, and hence the power in first beam 16 from laser 12;

$M_{13A}$ is a proportionality constant which depends upon factors such as the magnitude of the optogalvanic effect for the particular transition associated with the first wavelength, the configuration of chamber 32a; and the sensitivity of the detector in unit 42a, associated with chamber 32a. Proportionality constant $M_{13A}$ also depends, to some extent, on the proportion of $^{13}CO_2$ in the excited state within chamber 32a, which in turn depends on the excitation power supplied to coil 40a and the configuration of the coil.

Similarly, the second signal magnitude for chamber 32b is given by:

$$S_{12A} = P_{12A} M_{12A} W_{12A} \quad (2)$$

Where:

$P_{12A}$ is the partial pressure or molecular concentration of $^{12}CO_2$ within chamber 32a;

$W_{12A}$ is the beam power at the second wavelength, and hence the power in second beam 18 from laser 14;

$M_{12A}$ is a proportionality constant which depends upon factors such as the magnitude of the optogalvanic effect for the particular transition associated with the second wavelength, the configuration of chamber 32a; and the sensitivity of the detector in unit 42a, associated with chamber 32a. Proportionality constant $M_{12A}$ also depends, to some extent, on the proportion of $^{12}CO_2$ in the excited state within chamber 32a, which in turn depends on the excitation power supplied to coil 40a and the configuration of the coil. For typical samples encountered during use of the instrument, the $^{12}CO_2$ concentration $P_{12A}$ is several times larger than the $^{13}CO_2$ concentration $P_{13A}$. Therefore, to provide signals $S_{13}$ and $S_{12A}$ of comparable magnitude, the beam power $W_{12A}$ at the second wavelength associated with $^{12}CO_2$ should be smaller than the beam power $W_{13A}$ at the first wavelength associated with $^{13}CO_2$. The arrangement of the optical components discussed above, which attenuates the beam from the second laser to a greater degree than the beam from the first laser, provides the desired power relationship in the combined beam.

Combining equations (1) and (2), the ratio $R_{13/12A}$ of $^{13}C$ to $^{12}C$ in the gas within chamber 32a is given by:

$$R_{13/12A} = \frac{P_{13A}}{P_{12A}} = \frac{S_{13A} M_{12A} W_{12A}}{S_{12A} M_{13A} W_{13A}} \quad (3)$$

Rearrangement of equation (3) gives:

$$1 = \frac{S_{13A} W_{12A}}{R_{13/12A} S_{12A} W_{13A}} K_A \quad (4)$$

Where $K_A$ is a further proportionality constant equal to the quotient of $M_{12A}$ and $M_{13A}$. The same equations apply with respect to each of the other chamber 32b, 32c and 32d, with the subscript A replaced to indicate the corresponding variables applying to chambers b, c and d. Because the combined light beam passes through all chambers simultaneously, and because net absorption within each chamber is negligible in comparison to the power in the beam, all of the chambers receive substantially the same ratio of optical power at the first and second wavelengths. Thus:

$$\frac{W_{12}}{W_{13}} = \frac{W_{12A}}{W_{13A}} = \frac{W_{12B}}{W_{13B}} = \frac{W_{12C}}{W_{13C}} = \frac{W_{12D}}{W_{13D}} \quad (5)$$

Equations 4 and 5 yield the relationship:

$$\frac{S_{13A} W_{12}}{R_{13/12A} S_{12A} W_{13}} K_A = \frac{S_{13B} W_{12}}{R_{13/12B} S_{12B} W_{13}} K_B = \quad (6)$$

$$\frac{S_{13C} W_{12}}{R_{13/12C} S_{12C} W_{13}} K_C = \frac{S_{13D} W_{12}}{R_{13/12D} S_{12D} W_{13}} K_D$$

Dividing by $\frac{W_{12}}{W_{13}}$ and rearranging terms, :

$$\frac{R_{13/12B}}{R_{13/12A}} = \frac{S_{13B} S_{12A}}{S_{13A} S_{12B}} \frac{K_B}{K_A} \quad (7)$$

$$\frac{R_{13/12C}}{R_{13/12A}} = \frac{S_{13C} S_{12A}}{S_{13A} S_{12C}} \frac{K_C}{K_A} \quad (8)$$

$$\frac{R_{13/12D}}{R_{13/12A}} = \frac{S_{13D} S_{12A}}{S_{13A} S_{12D}} \frac{K_D}{K_A} \quad (9)$$

For each standard cycle, all of the chambers are filled with the standard gas, and hence the left side in each of equations 7, 8 and 9 is unity. Thus, each of the ratios $$\frac{K_B}{K_A}, \frac{K_C}{K_A}, \frac{K_D}{K_A}$$

can be determined from the observed signals in a calibration cycle. When measurements are taken on a sample cycle a standard gas is employed in chamber 32a, and hence $R_{13}/12_A$ is the known ratio $R_{13/12S}$, where the subscript s indicates the standard gas. The ratio $R_{13/12}$ of $^{13}C$ to $^{12}C$ for the unknown sample in each chamber 32b, 32c and 32d can be deduced from the known ratio $R_{13/12S}$, the observed signals S and the ratios of calibration factors K determined on a calibration cycle. Computer 54 performs the calculations specified by the foregoing equations, and provides the results through output device 60. Provided that the calibration factors K remain constant for the various chambers, the results do not depend on the radiation power levels $W_{12}$ and $W_{13}$. Stated another way, the ratiometric calculation of equations 7–9 adjusts the value of $R_{13/12}$ for each unknown analyte based upon the results obtained for the known reference analyte in chamber 32a. That is, the calculation called for by equations 7–9 involves computation of a "double ratio" between (i) the ratio of response magnitudes for the two wavelengths for the unknown sample in a particular cell and (ii) the ratio of response magnitudes for the two wavelengths for the standard sample cell 32a. For example, in equation 9, the ratio $$\frac{S_{13D}S_{12A}}{S_{13A}S_{12D}}$$

is the double ratio between (i) the ratio of response magnitudes for the unknown sample $S_{13D}/S_{12D}$ and (ii) the ratio of response magnitudes for the standard sample $S_{13A}/S_{12A}$. Effects caused by changes in the applied radiation and other variations in the system cancel one another in computation of the double ratio. The standard gas acts as an internal calibration standard during each sample cycle, and the results of this internal calibration are incorporated in the double ratio.

Preferably, the lasers used in the system are stabilized so as to minimize variation in the wavelengths of light emitted by the lasers. Such variation in wavelength can occur, for example, as the temperatures of the lasers change. Variation in the wavelength of the light emitted by one laser will alter the optogalvanic effect of the light from such laser. The further the wavelength of the light is from the exact transition energy, the lower the optogalvanic effect. To a first approximation, this effect is corrected by the system in much the same way as variations in the power level of the lasers. Thus, to the extent that the variation affects all of the parameters K in equations 7–9 similarly, the variation will not affect the calculated value of the isotopic ratio in the unknown sample. However, it is still desirable to maintain each laser at a substantially constant wavelength. The discharge tubes of the lasers should be maintained under controlled temperatures. For example, the apparatus may incorporate a vessel for holding a fluid, preferably a liquid, and a temperature controller for maintaining the fluid at a constant temperature and circulating the fluid within the vessel. The discharge tubes of the lasers may be mounted within the vessel and bathed in the fluid. Also, the wavelengths of the lasers can be stabilized by means of a feedback control arrangement in which the optogalvanic effect caused by radiation from each laser in the standard gas is monitored and each laser is tuned in response to the results of such monitoring to maintain this optogalvanic effect at a constant level.

Numerous variations and combinations of the features described above can be utilized without departing from the present invention. For example, although the use of a single beam path as described above, such that the radiation is directed through all of the samples in order, is greatly preferred, other optical arrangements could be employed to direct light from a source through plural samples simultaneously. For example, optical elements such as couplers or beam splitters which direct light from one or more laser beams onto plural paths to several samples simultaneously can be employed. Provided that these optical elements maintain fixed portions of the applied optical power onto each sample, the composition of each sample can be determined in a manner similar to that described above, using a reference sample exposed simultaneously with the other samples as an internal calibration standard. Also, apparatus and methods according to the present invention can be used for analyses other than the $CO_2$ isotopic content analysis discussed above. The path of the beam through the sample containers need not be a straight line; the path can be folded if appropriate optical components are provided to deflect the beam. As these and other variations and combinations of the features discussed above can be utilized, the foregoing description of the preferred embodiments should be taken by way of illustration rather than by way of limitation of the invention as defined by the claims.

What is claimed is:

1. A method of analyzing an analyte comprising the steps of:
    (a) maintaining a plurality of separate samples of said analyte;
    (b) directing radiation including a plurality of wavelengths corresponding to transition energies of a plurality of species which may be present in said analyte through said plural samples so that the radiation passes from a common source of radiation through all of the samples simultaneously, whereby all of said samples will be exposed to radiation of substantially the same spectral composition; and
    (c) monitoring response of said samples to said radiation to determine a response for each of said wavelengths; and
    (d) comparing the responses of each said sample for said wavelengths to one another to produce a measure of the relative abundances of said species in each said sample.

2. A method as claimed in claim 1 wherein said plural samples include at least one reference sample having known composition and at least one unknown sample, the method further comprising the step of adjusting said measure for each unknown sample based upon the responses for said reference sample.

3. A method as claimed in claim 1 wherein said at least one species to be detected includes a first species and a second species, said radiation includes first and second wavelengths corresponding to transition energies of said first and second species, respectively, said step of computing a measure of abundance including the step of computing a ratio of abundances of said first and second species in each said unknown sample.

4. A method as claimed in claim 3 wherein said step of computing said ratio of abundances includes the step of computing a double ratio equal to a ratio between (i) an unknown-sample response ratio between the magnitudes of the responses of said unknown sample to said first and second wavelengths for each said unknown sample, and (ii) a standard-sample response ratio between the magnitudes of the responses of said standard sample to said first and second wavelengths for said standard sample.

5. A method as claimed in claim 1 wherein said step of directing radiation includes the step of directing one or more beams of radiation through all of said samples in an upstream-to-downstream order.

6. A method as claimed in claim 5 wherein said step of directing radiation includes the step of providing all of said wavelengths in a single beam of radiation and directing said single beam of radiation through all of said samples in said upstream-to-downstream order.

7. A method as claimed in claim 6 wherein said step of providing all of said wavelengths in a single beam includes the step of combining a plurality of beams of different spectral composition from a plurality of sources to form said single beam.

8. A method as claimed in any one of claim 5 or claim 6 or claim 7 wherein said step of monitoring responses is performed by monitoring an induced effect in each of said samples.

9. A method as claimed in claim 8 wherein said step of maintaining said samples includes the step of maintaining said samples in condition wherein each said species is present in an excited state, said wavelengths corresponding to transition energies of said species in said excited states.

10. A method as claimed in claim 9 wherein said step of maintaining said samples includes the step of maintaining each said sample in a plasma and said step of monitoring the induced effect includes monitoring electrical impedance of each said plasma to thereby detect optogalvanic effect induced by said radiation.

11. A method of analyzing an analyte including at least one species to be detected comprising the steps of:
    (a) maintaining a plurality of separate samples of said analyte;
    (b) directing radiation including a wavelength corresponding to a transition energy of each species to be detected through said plural samples by directing one or more beams of radiation through all of said samples in an upstream-to-downstream order, and
    (c) monitoring an induced effect in said samples caused by said radiation to determine a response for each said sample to each said wavelength.

12. A method as claimed in claim 11 wherein said plural samples include at least one reference sample having known composition and at least one unknown sample, the method further comprising the step of computing a measure of the abundance of each said species in each said unknown sample based upon the response or responses for said reference sample and the response or responses for said unknown sample.

13. A method as claimed in claim 12 wherein said at least one species to be detected includes a first species and a second species, said radiation includes first and second wavelengths corresponding to transition energies of said first and second species, respectively, said step of computing a measure of abundance including the step of computing a ratio of abundances of said first and second species in each said unknown sample.

14. A method as claimed in claim 13 wherein said step of computing said ratio of abundances includes the step of computing a double ratio equal to a ratio between (i) an unknown-sample response ratio between the magnitudes of the responses of said unknown sample to said first and second wavelengths for each said unknown sample, and (ii) a standard-sample response ratio between the magnitudes of the responses of said standard sample to said first and second wavelengths for said standard sample.

15. A method as claimed in claim 12 wherein said step of directing one or more beams of radiation includes the step of providing a plurality of said wavelengths in a single beam of radiation and directing said single beam of radiation through all of said samples in said upstream-to-downstream order.

16. A method as claimed in claim 15 wherein said step of providing all of said wavelengths in a single beam includes the step of combining a plurality of beams of different spectral composition from a plurality of sources to form said single beam.

17. A method as claimed in claim 11 wherein said step of directing one or more beams of radiation includes the step of reflecting each said beam so that each beam passes through said samples in downstream-to-upstream order as well as in upstream-to-downstream order.

18. A method as claimed in claim 11 or claim 12 or claim 15 or claim 16 or claim 17 wherein said step of maintaining said samples includes the step of maintaining each said sample in a condition wherein each said species to be detected is present in an excited state.

19. A method as claimed in claim 18 wherein each said sample is maintained in a plasma and said step of monitoring an induced effect includes monitoring electrical impedance of each said plasma to thereby detect optogalvanic effects induced by said radiation.

20. Analytical apparatus comprising:
    (a) a frame;
    (b) a plurality of chambers mounted to said frame along a path, each such chamber having upstream and downstream end walls facing in upstream and downstream directions along said path;
    (c) irradiation means for providing radiation at one or more wavelengths corresponding to transition energies of species in an analyte and directing said radiation along said path so that said radiation passes through said chambers in series; and
    (d) detection means for monitoring an induced effect in analyte disposed within each said chamber to said radiation so as to monitor the response of each said analyte to radiation at each said wavelength.

21. Apparatus as claimed in claim 20 further comprising excitation means for maintaining an analyte in each said chamber in an excited condition such that one or more species in said analyte are present in excited states.

22. Apparatus as claimed in claim 21 wherein said excitation means includes means for maintaining analyte in each said chamber as a plasma.

23. Apparatus as claimed in claim 22 wherein said detection means includes means for detecting the electrical impedance of the plasma in each said chamber.

24. Apparatus as claimed in claim 20 wherein said loading means includes means for loading separate analytes into a plurality of said chamber simultaneously.

25. Apparatus as claimed in claim 24 wherein said loading means includes a source of a standard analyte and means for loading the standard into one of said chambers and loading analytes of unknown composition into others of said chambers.

26. Apparatus as claimed in claim 20 wherein said path has upstream and downstream ends, said chambers being arranged in upstream-to-downstream order on said path, and wherein said irradiation means includes means for directing a beam of radiation along the path from the upstream end to the downstream end, and a mirror for reflecting the beam from the downstream end to the upstream end.

27. Apparatus as claimed in claim 20 wherein said irradiation means includes first and second lasers and combining optics for combining beams of radiation from said first and second lasers to form a composite beam, said combining optics being adapted to attenuate the beam from said second laser to a greater extent than the beam from said first laser.

* * * * *

UNITED STATES PATENT AND TRADEMARK OFFICE
CERTIFICATE OF CORRECTION

PATENT NO. : 5,818,580
DATED : October 6, 1998
INVENTOR(S) : Murnick

It is certified that error appears in the above-identified patent and that said Letters Patent is hereby corrected as shown below:

Column 12, line 13, "$S_{13}$" should read --$S_{13A}$--.

Signed and Sealed this

Second Day of March, 1999

Attest:

Q. TODD DICKINSON

*Attesting Officer*  *Acting Commissioner of Patents and Trademarks*